US008897516B2

(12) United States Patent
Turgeman (10) Patent No.: US 8,897,516 B2
(45) Date of Patent: Nov. 25, 2014

(54) TWO-DIMENSIONAL CARDIAC MAPPING

(75) Inventor: Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 167 days.

(21) Appl. No.: 13/049,315

(22) Filed: Mar. 16, 2011

(65) Prior Publication Data

US 2012/0237093 A1 Sep. 20, 2012

(51) Int. Cl.
*G06K 9/00* (2006.01)
*A61B 5/042* (2006.01)

(52) U.S. Cl.
CPC .................................. *A61B 5/0422* (2013.01)
USPC ........... 382/128; 382/131; 382/132; 382/154; 382/139

(58) Field of Classification Search
USPC .................................. 382/128, 139, 140, 151
See application file for complete search history.

(56) References Cited

U.S. PATENT DOCUMENTS

2005/0228252 A1   10/2005  Neason
2006/0064006 A1*  3/2006   Strommer et al. ............ 600/415
2008/0188765 A1*  8/2008   Stolarski et al. ............. 600/518
2009/0148012 A1*  6/2009   Altmann et al. ............. 382/128
2010/0331950 A1*  12/2010  Strommer .................... 623/1.11

FOREIGN PATENT DOCUMENTS

WO            93/13708 A1    7/1993
WO     WO 2007/066096 A2    6/2007
WO     WO 2008/135731 A1   11/2008

OTHER PUBLICATIONS

Desjardins, B., et al. "Infarct Architecture and Characteristics on Delayed Enhanced Magnetic Resonance Imaging and Electroanatomic Mapping in Patients with Postinfarction Ventricular Arrhythmia", May 2009, Heart Rhythm, vol. 6, No. 5., pp. 644-651.
Extended European Search Report dated May 29, 2012 from related European Application No. 12 15 9569.8.

* cited by examiner

*Primary Examiner* — Matthew Bella
*Assistant Examiner* — Weiwen Yang (57) ABSTRACT

A method consisting of formulating a one-to-one correspondence between locations on a three-dimensional surface of a body cavity and coordinates in a two-dimensional coordinate frame representative of the locations. The method also includes recording respective time-varying electrical potentials at the locations. The method further includes displaying a map of the two-dimensional coordinate frame, and presenting respective graphic representations of the time-varying electrical potentials at positions in the map corresponding to the coordinates of the locations.

19 Claims, 6 Drawing Sheets

TWO-DIMENSIONAL CARDIAC MAPPING

FIELD OF THE INVENTION

The present invention relates generally to cardiac electrophysiology, and specifically to visualizing the cardiac electrophysiological behavior.

BACKGROUND OF THE INVENTION

Displaying electrophysiology (EP) data of a beating heart in an intelligible and clear manner is a daunting task. Even ignoring the motion due to the beating, the EP data changes over time in both magnitude and position, and the changes are relatively quick. In addition, the EP data occurs in three dimensions.

PCT application WO/2008/135731, to Francis et al., whose disclosure is incorporated herein by reference, describes a method of generating a model of a cardiac surface. The method comprises measuring an electrogram voltage at a plurality of points within a heart, and generating images representing each electrogram voltage.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

An embodiment of the present invention provides a method, including:

formulating a one-to-one correspondence between locations on a three-dimensional surface of a body cavity and coordinates in a two-dimensional coordinate frame representative of the locations;

recording respective time-varying electrical potentials at the locations;

displaying a map of the two-dimensional coordinate frame; and presenting respective graphic representations of the time-varying electrical potentials at positions in the map corresponding to the coordinates of the locations.

Typically, the method includes inserting a distal tip of a probe having an electrode into the body cavity, and recording the time-varying potentials includes using the electrode to record the potentials. The method may also include determining the locations on the three-dimensional surface using the electrode.

In a disclosed embodiment the map includes markings corresponding to features of the three-dimensional surface.

In an alternative disclosed embodiment the map includes annotations descriptive of elements of the three-dimensional surface.

In a further disclosed embodiment the graphic representations include rectangular bars having lengths selected in response the electrical potentials. Alternatively or additionally, the graphic representations include bars having colors selected in response the electrical potentials.

The method may include presenting information concerning the body cavity, other than the graphic representations, on the map.

In an alternative embodiment displaying the map includes selecting a section of the body cavity, and presenting the graphic representations only for the section. Typically, the selecting includes choosing from a group including manual selection, semi-automatic selection, and automatic selection.

In a further alternative embodiment presenting the respective graphic representations of the time-varying electrical potentials includes selecting a window of the potentials, and presenting the representations in response to the window. Typically, the method includes selecting a section of the body cavity, and presenting the graphic representations of the window only for the section.

In a yet further alternative embodiment the method includes delineating a path followed by the time-varying electrical potentials in the body cavity, and displaying the path on the map. Typically, the method further includes presenting the graphic representations of the potentials only for the path.

There is further provided, according to an embodiment of the present invention, apparatus, including:

a controller, configured to:

formulate a one-to-one correspondence between locations on a three-dimensional surface of a body cavity and coordinates in a two-dimensional coordinate frame representative of the locations, and record respective time-varying electrical potentials at the locations; and a screen, coupled to the controller, and configured to:

display a map of the two-dimensional coordinate frame, and present respective graphic representations of the time-varying electrical potentials at positions in the map corresponding to the coordinates of the locations.

There is further provided, according to an embodiment of the present invention, a computer software product including a non-transitory computer-readable medium having computer program instructions recorded therein, which instructions, when read by a computer, cause the computer to:

formulate a one-to-one correspondence between locations on a three-dimensional surface of a body cavity and coordinates in a two-dimensional coordinate frame representative of the locations;

record respective time-varying electrical potentials at the locations;

display a map of the two-dimensional coordinate frame; and present respective graphic representations of the time-varying electrical potentials at positions in the map corresponding to the coordinates of the locations.

The present disclosure will be more fully understood from the following detailed description of the embodiments thereof, taken together with the drawings, in which:

DETAILED DESCRIPTION OF EMBODIMENTS

Overview

An embodiment of the present invention provides a method for viewing time-varying electrophysiological potentials of the three-dimensional (3D) surface of a body cavity, such as one or more chambers of the heart. The method allows simultaneous viewing of the potentials, regardless of the location on the surface at which the potentials are measured, while maintaining a visual correlation between the potentials and the locations.

A one-to-one correspondence between the 3D locations and coordinates in a two-dimensional coordinate frame representative of the locations is formulated and a map of the two-dimensional coordinate frame is displayed on a screen. The potentials are recorded at various locations of the 3D surface. During playback of the potentials, graphic representations, typically bars having a varying length and/or a varying color that corresponds to a value of the time-varying potentials, are presented on the map at positions corresponding to the coordinates of the locations.

By converting the 3D surface to a two-dimensional map, all locations on the surface, and associated elements such as the representations of potentials described above, may be viewed simultaneously, without any manipulation of the map. This is in contrast to viewing an unconverted 3D surface with associated representations. In this case the 3D nature of the body cavity surface prevents simultaneous viewing of all surface locations, and typically requires rotating the surface in order to view all the locations and their associated representations.

System Description

Figure 1:
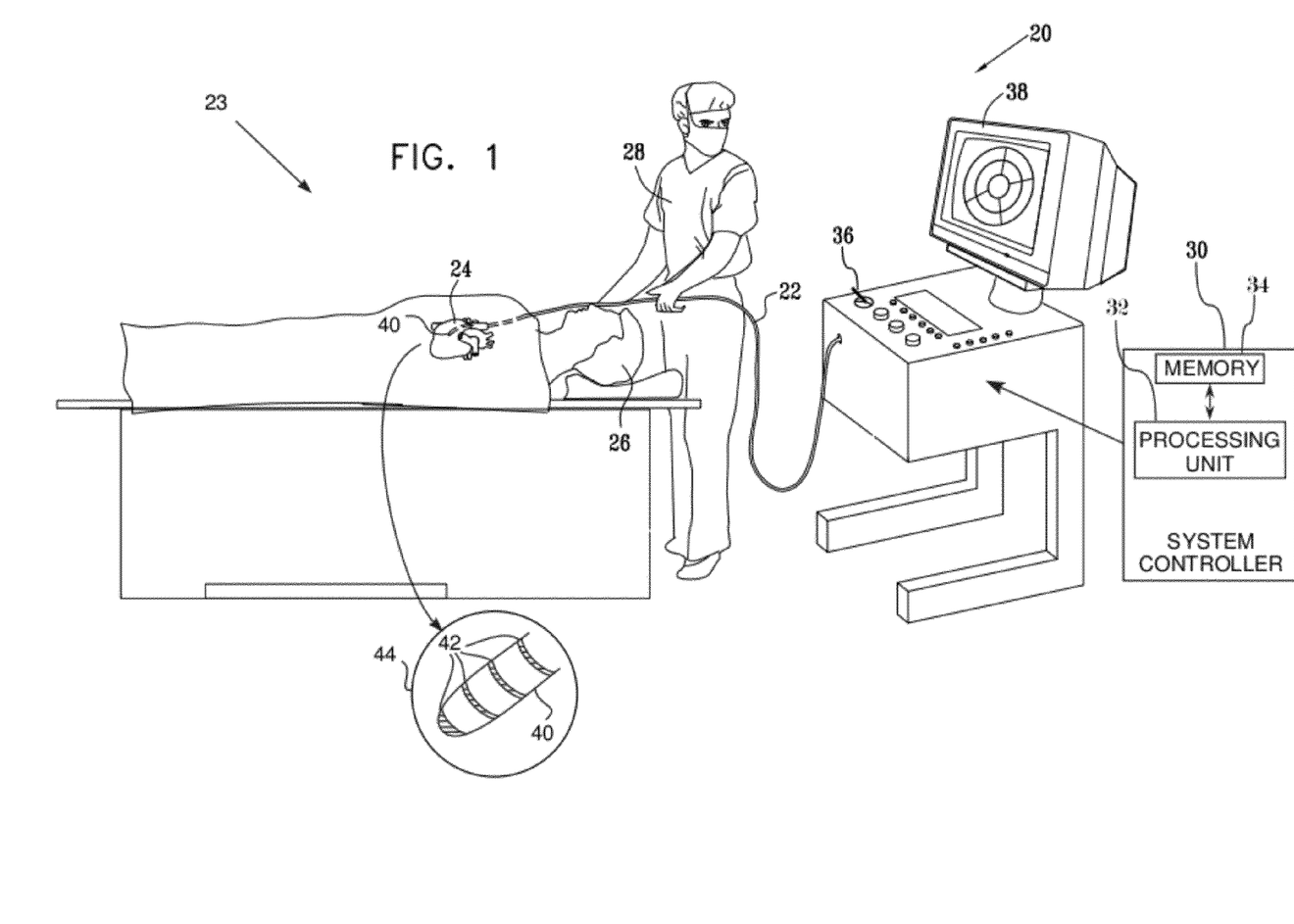
FIG. 1 is a schematic, pictorial illustration of a cardiac electrophysiology (EP) system, according to an embodiment of the present invention.

Reference is now made to FIG. 1, which is a schematic, pictorial illustration of a cardiac electrophysiology (EP) system 20, according to an embodiment of the present invention. In system 20, a probe 22 is inserted into a body cavity 23, such as a chamber of a heart 24, of a subject 26. Typically, the probe is used by a medical practitioner 28 during an investigative medical procedure performed on subject 26.

The functioning of system 20 is managed by a system controller (SC) 30, comprising a processing unit 32 communicating with a memory 34, wherein is stored software for operation of system 20. Controller 30 is typically an industry-standard personal computer (PC) comprising a general-purpose computer processor. However, in some embodiments, at least some of the functions of the controller are performed using custom-designed hardware and software, such as an application specific integrated circuit (ASIC) or a field programmable gate array (FPGA). Controller 30 is typically operated by practitioner 28 using a pointing device 36 and a graphic user interface (GUI) on a screen 38, the device and the GUI enabling the practitioner to set parameters of system 20. Screen 38 typically also displays results, via the GUI, of the procedure to the medical practitioner.

The software in memory 34 may be downloaded to the controller in electronic form, over a network, for example. Alternatively or additionally, the software may be provided on non-transitory tangible media, such as optical, magnetic, or electronic storage media.

Probe 22 is configured to measure electrophysiological potentials of heart tissue over time, using one or more electrodes 42 located on a distal tip 40 of the probe, as illustrated in a magnified section 44 of FIG. 1. The one or more electrodes may be used for other purposes as well, such as for tracking a location and/or an orientation of the distal tip. Electrodes 42 are connected by wires (not shown) in probe to driver and measurement circuitry in system controller 30.

Alternatively or additionally, the location and/or the orientation of the distal tip may be ascertained by other systems known in the art, for example, by a magnetic tracking system. One such magnetic tracking system is the CARTO 3 system, produced by Biosense Webster, Inc, Diamond Bar, Calif., which tracks the distal tip by using alternating magnetic fields to induce corresponding positioning currents in coils in the tip.

During the investigative medical procedure referred to above, practitioner 28 positions probe 22 at a number of locations in heart 24 to measure the electrical potentials at the locations. Typically, at each location the practitioner uses controller 30 to record the electrical potential as it varies in time, together with the times. Alternatively or additionally, the practitioner positions multiple probes, substantially similar to probe 22, at some of the different locations, so as to be able to measure and record the potentials and times at these locations substantially simultaneously.

While the number of locations at which the potential is measured is typically of the order of 100, embodiments of the present invention are not limited to the number of locations, and so comprise numbers of locations smaller and larger than 100. For simplicity and clarity, the following description considers the results from six locations, and those having ordinary skill in the art will be able to adapt the description for other numbers of locations.

Figure 2:
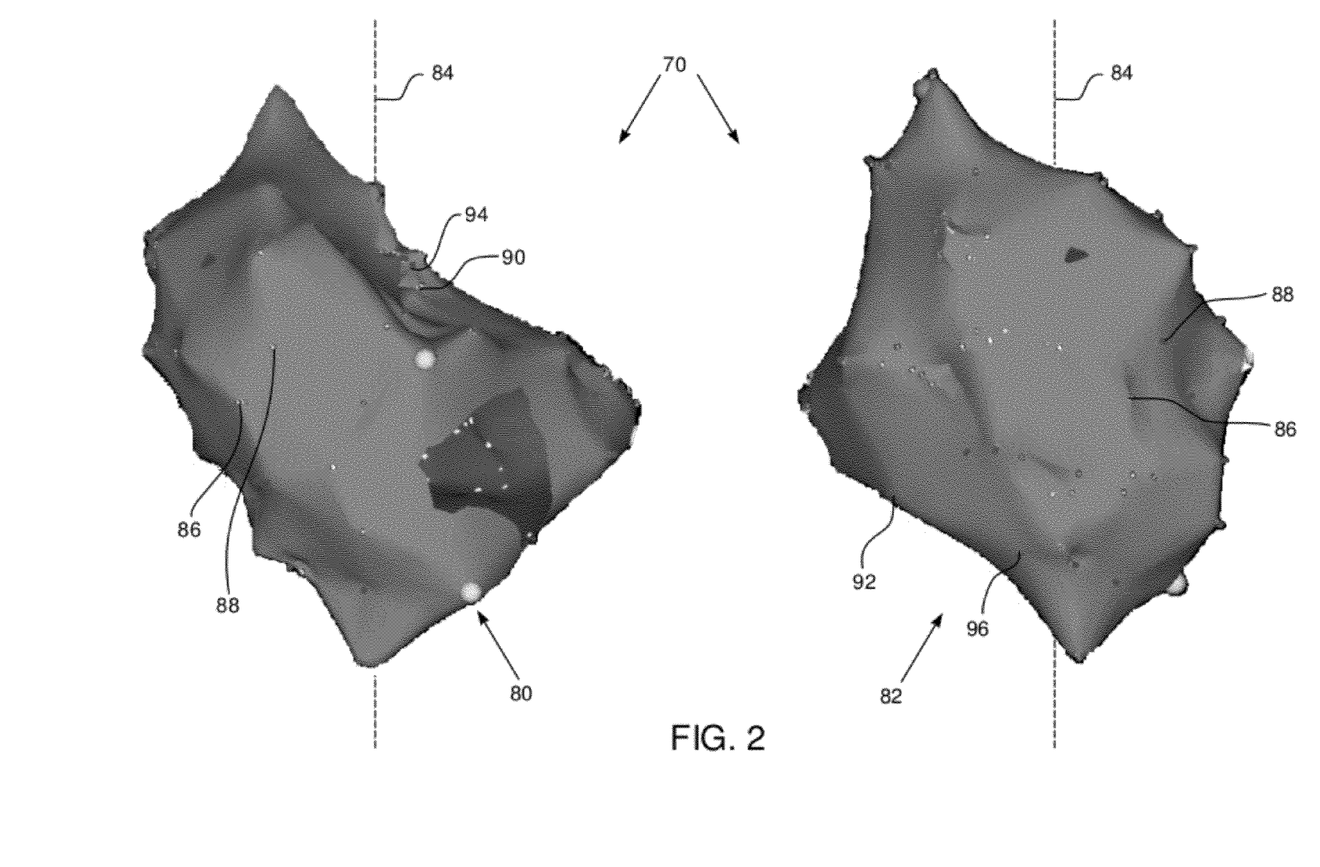
FIG. 2 is a schematic diagram illustrating two different views of elements of a heart, according to an embodiment of the present invention.

FIG. 2 is a schematic diagram illustrating two different views of elements of heart 24, according to an embodiment of the present invention. The diagram shows representations of a three-dimensional (3D) interior surface 70 of heart 24. The representations are generated by using distal tip 40 to establish locations in space of the surface, using one of the tracking systems referred to above. The locations are recorded by system controller 30, which uses the locations, typically with an interpolation procedure, to formulate a 3D map of the surface.

A view 80 shows 3D surface 70 from a first viewpoint, and a view 82 shows the surface from a second viewpoint. View 80 is herein also referred to as frontal view 80. View 82, also herein referred to as side view 82, is related to frontal view 80 by being rotated approximately 90° around a vertical axis 84. The direction of rotation is counter-clockwise looking down along the axis. The rotation moves the points of the surface in the two viewpoints, so that some points remain visible in both viewpoints, but some are only visible in one of the viewpoints.

For example points 86 and 88 are on the left of axis 84 in the frontal view, and rotate to the right of axis 84 in the side view. Points 90 and 94 are visible, at the right of axis 84, in the frontal view, but are not visible in the side view, and points 92 and 96 are not visible in the frontal view, but become visible, because of the rotation, in the side view.

Figure 3:
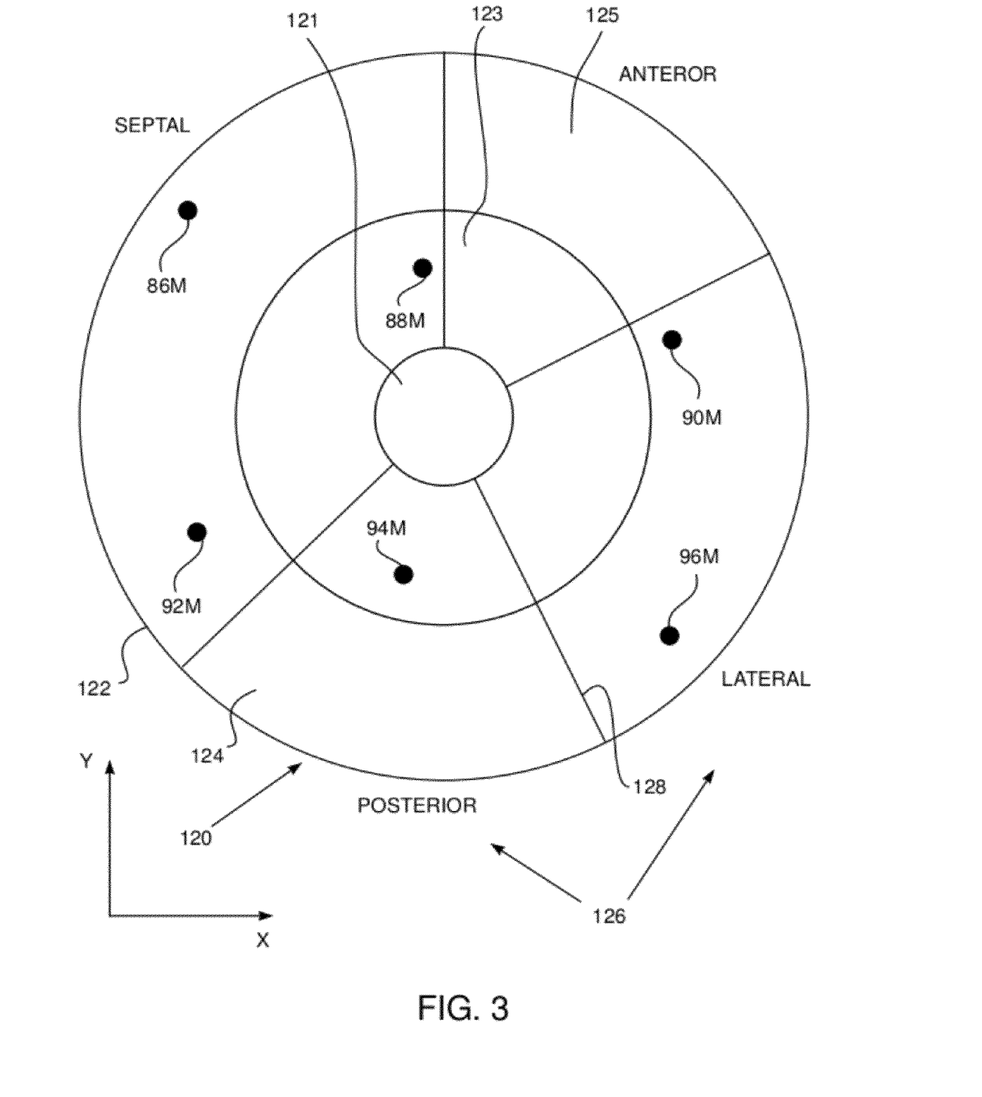
FIG. 3 is a schematic diagram of a two-dimensional (2D) map, according to an embodiment of the present invention.

FIG. 3 is a schematic diagram of a two-dimensional (2D) map 120, according to an embodiment of the present invention. Map 120 is a two-dimensional projection of 3D surface 70, so that every location on the 3D surface maps in a oneto-one correspondence to a respective, different point, on 2D map 120. Map 120 is formulated in a two-dimensional coordinate frame having orthogonal x and y axes, and each of the points of the map have respective coordinates in the frame. By way of example, points 86, 88, 90, 92, 94, and 96 of surface 70 map to respective different points 86M, 88M, 90M, 92M, 94M, and 96M on map 120. The one-to-one correspondence, or mapping, between the points on the 3D surface and map 120 may be by any mathematical function transforming coordinates of the 3D surface to two-dimensional coordinates, or ordered (x, y) pairs, defining 2D map 120.

By way of example, a perimeter 122 of map 120 is shown as being circular, but in alternative embodiments of the present invention the map may have any convenient two-dimensional perimeter, including curved and straight linear sections. An interior region 124 within perimeter 122 is assumed, by way of example, to be a single contiguous area, completely filling the perimeter. However, in other embodiments, interior region 124 comprises more than one contiguous area. Each such area may or may not contact other such areas within region 124. In all cases, each point in perimeter 122 and region 124 maps in a one-to-one correspondence with a respective point of 3D surface 70.

By way of example, map 120 may be considered as a geometrical projection onto a plane at right angles to an axis between the apex of the heart and the center of the left ventricle. In the illustration the map has been divided into nine regions formed as three concentric sub-regions: an apical central region 121, a middle region 123, and a basal, outer region 125. Moving from region 121 to perimeter 122 corresponds to moving from the apex to the base of the left ventricle. This division, as will be apparent to those of ordinary skill in the art, is consistent with the common artery blood supply, However, any other convenient division of map 120 may be used, or the map may not be subdivided.

Map 120 is displayed on screen 38. Typically, annotations 126, such as "anterior" and "posterior," may be placed on or besides the map, to assist practitioner 28 in associating elements of map 120 with corresponding elements of 3D surface 70. The annotations are typically descriptive of the associated elements. Alternatively or additionally, interior region 124 may comprise map markings 128, such as lines and/or shadings and/or colorations to correspond with features such as scars or boundaries or delineations of surface 70.

Figure 4:
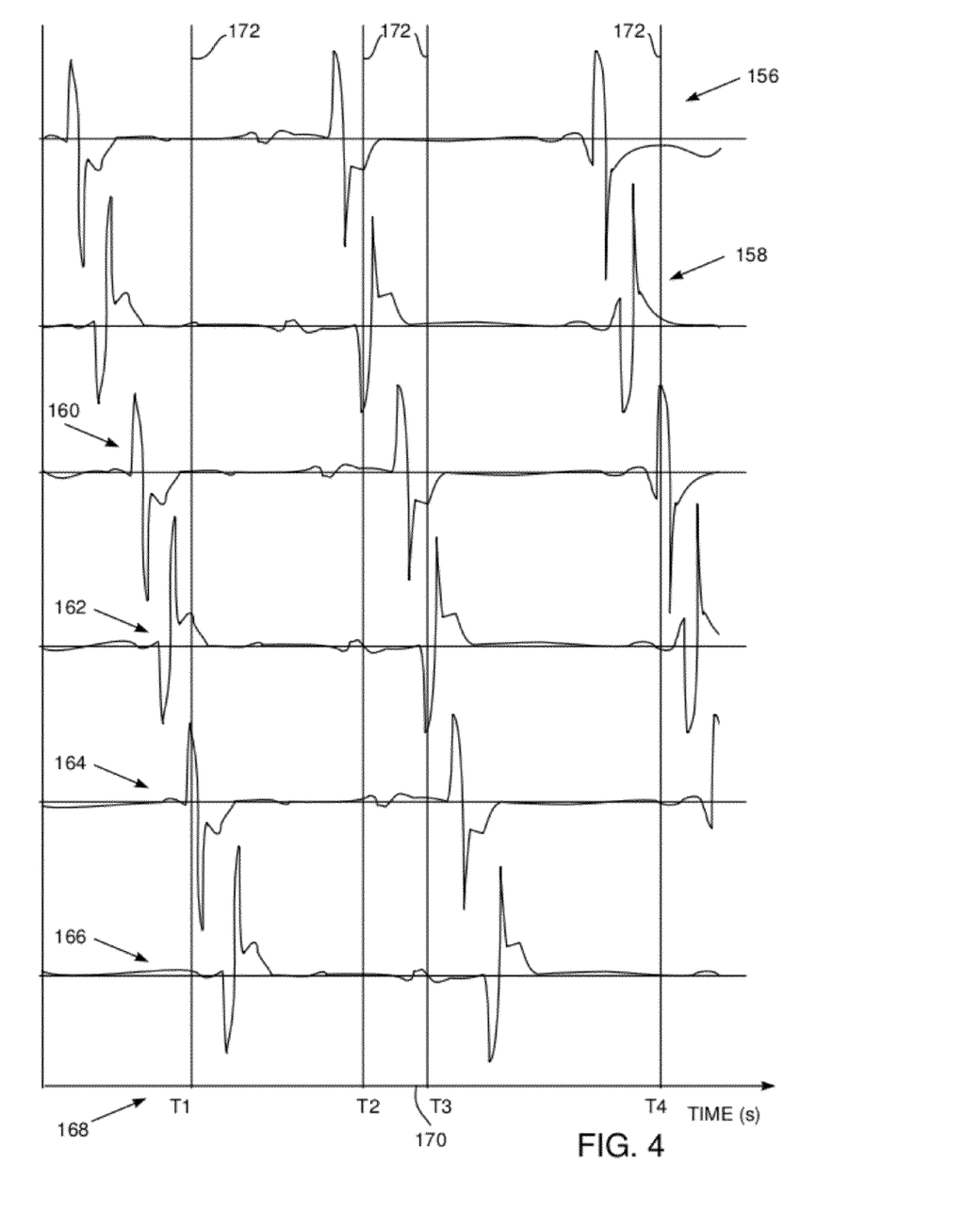
FIG. 4 is a schematic diagram of voltage vs. time graphs, according to an embodiment of the present invention.

FIG. 4 is a schematic diagram of voltage vs. time graphs, according to an embodiment of the present invention. Typically, while data for 3D surface 70 of heart 24 is being assembled by operator moving the probe to contact surfaces of the heart, as described above, the probe measures potentials at the points of contacts. For each point where the potentials are measured, controller 30 records a set of potentials and corresponding times, and stores the set in memory 34. Alternatively or additionally, sets of potentials and times for points on surface 70 may be recorded and stored in memory 34 independently of the assembly of location data for the 3D surface.

In the following description, controller 30 is assumed to record investigative sets of potentials and times for points 86, 88, 90, 92, 94, and 96. The recordings may be made sequentially. Alternatively or additionally, in the case of the use of multiple probes, at least some of the recordings may be made simultaneously. Typically, during recording of a given investigative set of potential/time readings, controller records a reference set of potential/time readings using another probe. The reference set may be taken by positioning the probe in the coronary sinus, or at any other convenient position of the heart generating repetitive electrophysiological signals. Alternatively or additionally, any other cardiac related signals may be used as a reference set, such as body surface electrocardiograph signals.

After the controller has recorded the investigative potential/time sets, the records may be gated using the reference set of readings. The gating translates the investigative sets in time, so that each set of records has a common time axis, and is converted to a respective gated set of records. The gated investigative sets of records are stored in memory 34. Graphs 156, 158, 160, 162, 164, and 166, herein also referred to collectively as graphs 168, are graphical displays of the gated investigative sets of readings for points 86, 88, 90, 92, 94, and 96 respectively. Graphs 168 have a common time axis 170.

Practitioner 28 replays the gated records by traversing along time axis 170, so that as each time on the axis is reached, controller 30 recalls respective potentials for each point of contact that has been stored in memory 34. In the case of the six points of contact 86, 88, 90, 92, 94, and 96 assumed above at each instant in time the controller recalls six potentials. The time traversal may be conveniently illustrated on graphs 168 by a moving vertical line 172. The replay of the gated records may be manual, by the practitioner effectively moving the position of line 172 on the time axis. Alternatively, the replay of the gated records may be implemented by controller 30 moving line 172 automatically on the time axis, typically repetitively. By way of example, line 172 is shown at four different times T1, T2, T3, and T4.

Figure 5:
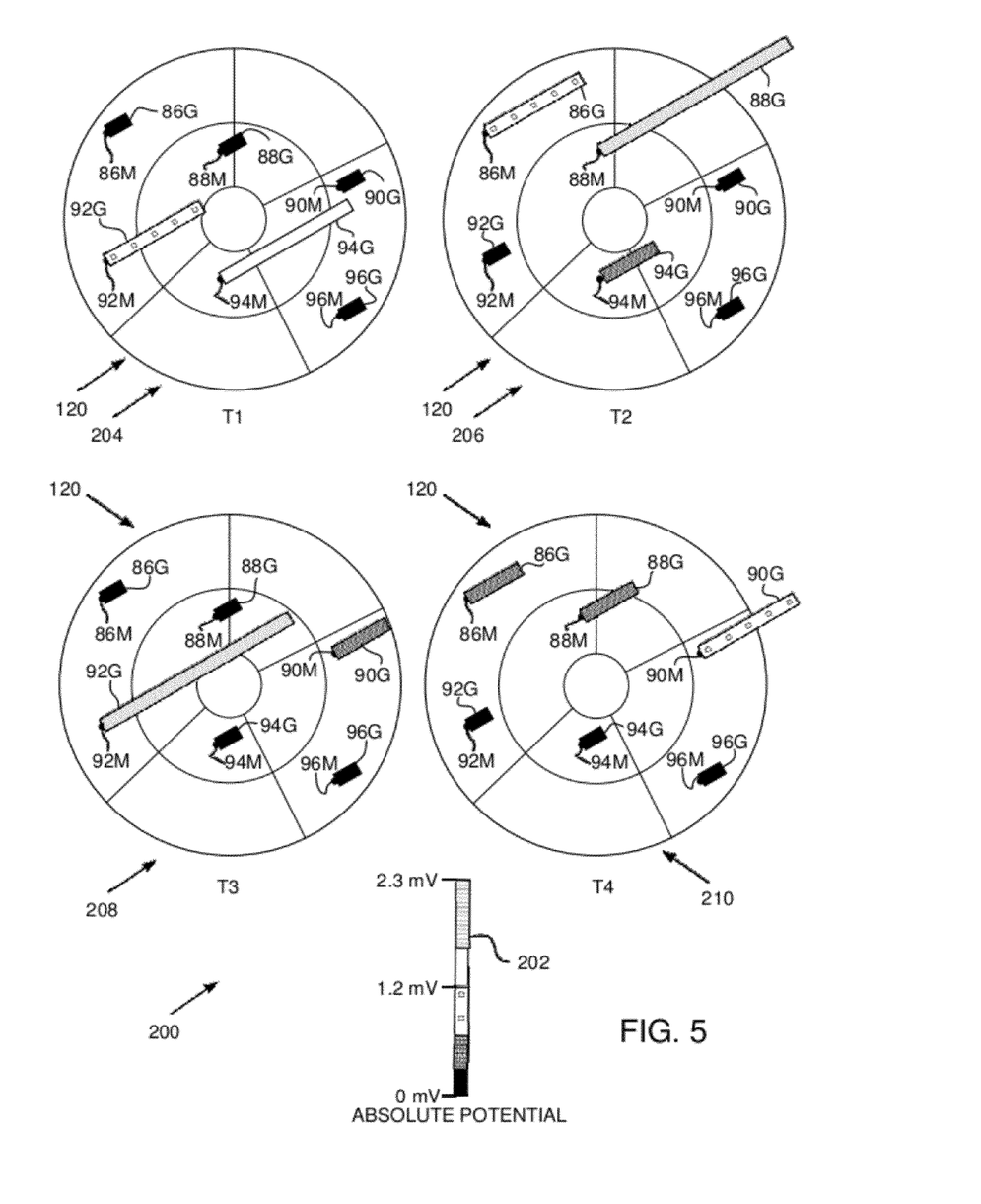
FIG. 5 is a schematic diagram illustrating graphic displays of the replay of gated records, according to an embodiment of the present invention.

As explained above, the gated records comprise records of potentials vs. times for selected points of surface 70. In displays 200, 2D map 120 is used as a basis for the replay, and graphic representations or symbols, representative of the recorded potentials for particular points, are coupled to the respective point on the 2D map. The graphic symbol is selected to be uniquely representative of the potential level.

In a first embodiment, the graphic symbol comprises a rectangular bar, the length of the bar being adjusted according to the level of the potential. In a second embodiment, the graphic symbol comprises a rectangular bar, a color of the bar changing according to the level of the potential. A third embodiment represents the potential by a rectangular bar wherein both the color and the length of the bar change according to the potential level. Typically, a reference scale, showing the relation between the graphic symbol and the potential level, is shown on screen 38.

The figure illustrates examples of a fourth embodiment, based on the graphs of FIG. 4. Respective graphic representations 86G, 88G, 90G, 92G, 94G, and 96G at points 86, 88, 90, 92, 94, and 96 display the different potentials at these points. Graphic representations 86G, 88G, 90G, 92G, 94G, and 96G are referred to collectively as representations 98G. Graphic representations 98G are bars having varying lengths and corresponding different shadings. The comparison between the potentials, bar lengths, and shadings is shown in a reference scale 202. A first diagram 204 corresponds to the potentials registered at time T1, and diagrams 206, 208, and 210 respectively correspond to the potentials at times T2, T3, and T4.

By way of example, the bars representing the potentials are displayed as parallel to each other, but not parallel to the x or y axes of map 120. However, the bars may be displayed in any convenient direction.

As is apparent from displays 200, at all times practitioner 28 is able to see the potentials generated by all points on surface 70, and to see all the potentials simultaneously. Furthermore, because the graphic representations of the potentials are coupled to the points generating the potentials, the practitioner is able to easily associate the potentials with the points. Thus, a "universal" view of all the potentials is available to the practitioner, without the practitioner having to manipulate map 120.

This is in contrast to the situation illustrated in FIG. 2, where, in order to view all the points on surface 70, the surface needs to be rotated. Similarly, if graphic representations of the potentials at the points are coupled to the points, at any instant in time, some of those representations will of necessity be hidden from view, because their coupled points are hidden from view.

Figure 6:
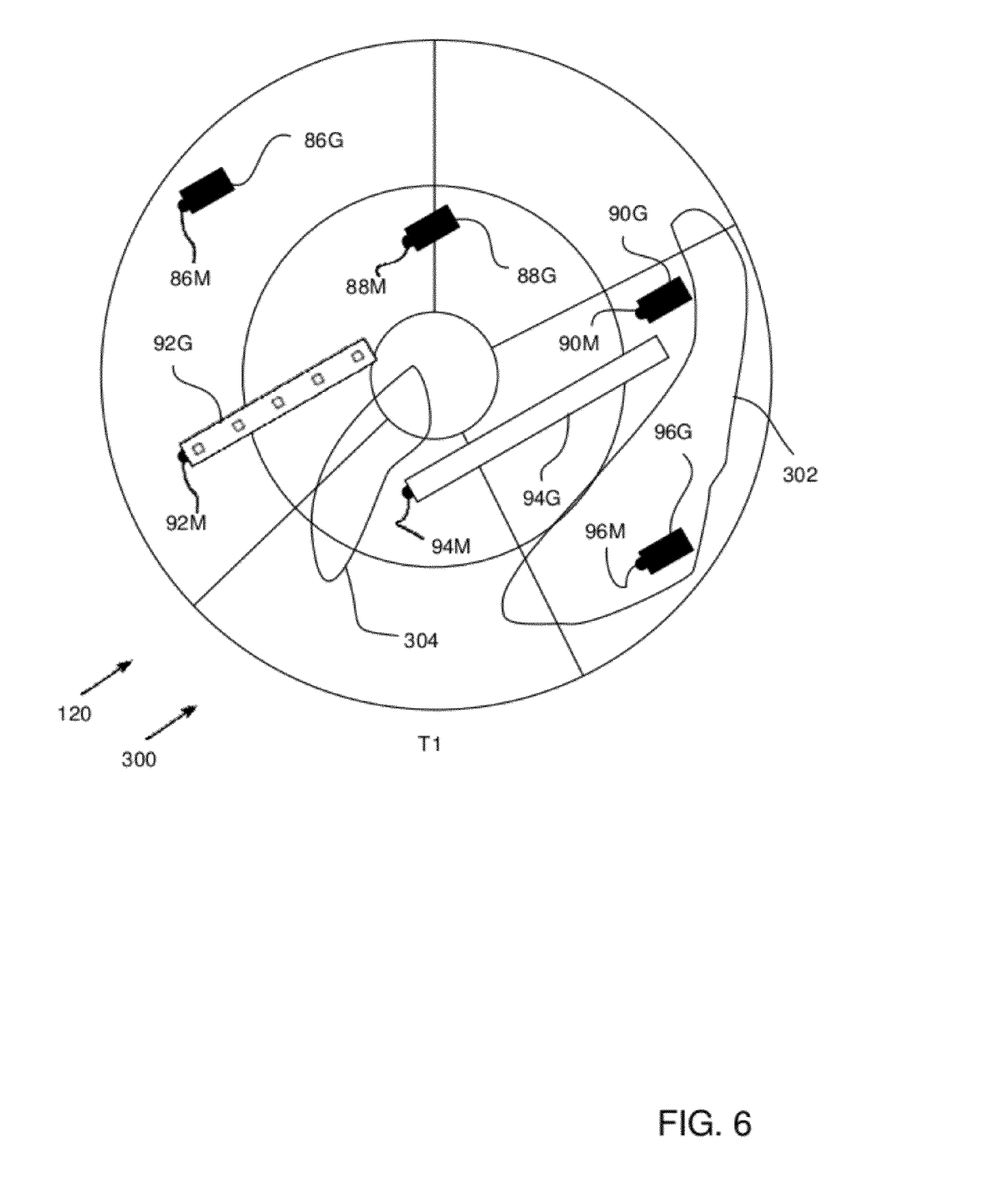
FIG. 6 is a schematic diagram illustrating an alternative graphic display of the replay of the gated records, according to an embodiment of the present invention.

FIG. 6 is a schematic diagram illustrating an alternative graphic display 300 of the replay of the gated records, according to an embodiment of the present invention. Apart from the differences described below, display 300 is generally similar to one of displays 200 (FIG. 5), and elements indicated by the same reference numerals in both display 300 and displays 200 are generally similar in construction and in operation. For simplicity, FIG. 6 only shows one diagram, corresponding to diagram 204 of FIG. 5.

Display 300, in addition to presenting the elements of diagram 204, presents further information concerning body cavity 23 that is relevant to the procedure being performed by practitioner 28. The information is incorporated into map 120. The other information illustrated in display 300 comprises isochronal potential lines 302 and 304 which are lines on map 120 indicating regions having, at a given time, equal voltages. Lines 320 and 304 translate to corresponding isochronal potential lines on surface 70. It will be understood that the isochronal lines illustrated in display 300 are examples of relevant information, other than that illustrated in diagram 204, which can be incorporated into map 120, so that embodiments of the present invention include incorporation of all such information into the map.

While the embodiment above have assumed that map 120 is of the whole heart, it will be understood that embodiments of the present invention comprise displaying a section of the heart, such as a portion containing scar tissue. The section displayed may be selected manually, semi-automatically, or automatically.

In an alternative embodiment, rather than the graphic representation displaying all values of the potential at a point, a window of potentials can be selected for display. Further alternatively, the graphic representation may be configured to display one particular value of potential.

It will be appreciated that the embodiments described above may be used to delineate and display paths, such as reentry and/or slow pathways followed by potentials in the heart.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A method, comprising:
    generating a plurality of three-dimensional representations of a surface of a body cavity by contacting a distal tip of a probe having an electrode on the surface of the body cavity and determining locations on the three-dimensional representations of the surface using the electrode, each representation being a different view of the same surface of the body cavity from a different viewpoint;
    measuring and recording respective time-varying electrical potentials at the locations on the three-dimensional representations of the surface of the body cavity in each of the different representations using the electrode;
    formulating a one-to-one correspondence between the locations on each of the different views of the three-dimensional representations of the surface of the body cavity and coordinates in a single two-dimensional coordinate frame representative of the locations;
    displaying a map of the one two-dimensional coordinate frame; and
    presenting respective graphic representations of the time-varying electrical potentials at positions in the map corresponding to the coordinates of the locations.

2. The method according to claim 1, wherein the map comprises markings corresponding to features of the three-dimensional representations of the surface.

3. The method according to claim 1, wherein the map comprises annotations descriptive of elements of the three-dimensional representations of the surface.

4. The method according to claim 1, wherein the graphic representations comprise rectangular bars having lengths selected in response the electrical potentials.

5. The method according to claim 1, wherein the graphic representations comprise bars having colors selected in response the electrical potentials.

6. The method according to claim 1, and comprising presenting information concerning the body cavity, other than the graphic representations, on the map.

7. The method according to claim 1, wherein displaying the map comprises selecting a section of the body cavity, and presenting the graphic representations only for the section.

8. The method according to claim 7, wherein the selecting comprises choosing from a group comprising manual selection, semi-automatic selection, and automatic selection.

9. The method according to claim 1, wherein presenting the respective graphic representations of the time-varying electrical potentials comprises selecting a window of the potentials, and presenting the representations in response to the window.

10. The method according to claim 9, and comprising selecting a section of the body cavity, and presenting the graphic representations of the window only for the section.

11. The method according to claim 1, and comprising delineating a path followed by the time-varying electrical potentials in the body cavity, and displaying the path on the map.

12. The method according to claim 11, and comprising presenting the graphic representations of the potentials only for the path.

13. Apparatus, comprising:
    a controller, configured to:
    generate a plurality of three-dimensional representations of a surface of a body cavity from a distal tip of a probe having an electrode in contact with the surface of the body cavity and determine locations on the three-dimensional representations of the surface in response to recordings from the electrode, each representation being a different view of the same surface of the body cavity from a different viewpoint;
    measure and record respective time-varying electrical potentials at the locations on the three-dimensional representations of the surface of the body cavity in each of the different representations using the electrode;
    formulate a one-to-one correspondence between the locations on each of the different views of the three-dimensional representations of the surface of the body cavity and coordinates in a single two-dimensional coordinate frame representative of the locations;

display a map of the single two-dimensional coordinate frame on a display screen; and present respective graphic representations of the time-varying electrical potentials at positions in the map corresponding to the coordinates of the locations.

14. The apparatus according to claim 13, wherein the map comprises markings corresponding to features of the three-dimensional representations of the surface.

15. The apparatus according to claim 13, wherein the map comprises annotations descriptive of elements of the three-dimensional representations of the surface.

16. The apparatus according to claim 13, wherein the graphic representations comprise rectangular bars having lengths selected in response the electrical potentials.

17. The apparatus according to claim 13, wherein the graphic representations comprise bars having colors selected in response the electrical potentials.

18. The apparatus according to claim 13, wherein the screen is configured to present information concerning the body cavity, other than the graphic representations, on the map.

19. A computer software product comprising a non-transitory computer-readable medium having computer program instructions recorded therein, which instructions, when read by a computer, cause the computer to:

generate a plurality of three-dimensional representations of a surface of a body cavity from a distal tip of a probe having an electrode in contact with the surface of the body cavity and determine locations on the three-dimensional representations of the surface in response to recordings from the electrode, each representation being a different view of the same surface of the body cavity from a different viewpoint;

measure and record respective time-varying electrical potentials at locations on the three-dimensional representations of the surface of the body cavity in each of the different representations using the electrode;

formulate a one-to-one correspondence between the locations on each of the different views of the three-dimensional representations of the surface of the body cavity and coordinates in a single two-dimensional coordinate frame representative of the locations;

display a map of the single two-dimensional coordinate frame; and present respective graphic representations of the time-varying electrical potentials at positions in the map corresponding to the coordinates of the locations.

* * * * *